(12) United States Patent
Sano et al.

(10) Patent No.: US 6,734,342 B2
(45) Date of Patent: May 11, 2004

(54) THEOBROMINE SYNTHASE POLYPEPTIDE OF COFFEE PLANT AND THE GENE ENCODING SAID POLYPEPTIDE

(75) Inventors: Hiroshi Sano, Ikoma (JP); Tomonobu Kusano, Nara (JP); Nozomu Koizumi, Ikoma (JP)

(73) Assignee: Nara Institute of Science and Technology, Ikoma (JP)

( * ) Notice: Subject to any disclaimer, the term of this patent is extended or adjusted under 35 U.S.C. 154(b) by 0 days.

(21) Appl. No.: 09/971,020

(22) Filed: Oct. 5, 2001

(65) Prior Publication Data

US 2002/0108143 A1 Aug. 8, 2002

(30) Foreign Application Priority Data

Oct. 6, 2000 (JP) .......................... 2000-307149

(51) Int. Cl.$^7$ ................... C12N 15/29; C12N 15/82; C12N 15/90; A01H 5/00; A01H 5/10
(52) U.S. Cl. ................ 800/285; 435/468; 536/23.6; 800/286
(58) Field of Search ................. 435/410, 419, 435/468; 536/23.6; 800/278, 285, 286, 295, 298

(56) References Cited

FOREIGN PATENT DOCUMENTS

| EP | 1 055 727 A | 11/2000 | ........... C12N/15/12 |
| EP | 1055727 A2 * | 11/2000 | ........... C12N/15/12 |
| WO | WO 97/35960 | 10/1997 | |

OTHER PUBLICATIONS

Ogita et al., Nature, 2003, vol. 423, p. 823.*
Zubieta et al., Plant Cell, Aug. 2003, vol. 15, pp. 1704–1716.*
Ogawa et al, "7–Methylxanthine methyltransferase of Coffee Plants", 2001, The Journal of Biological Chemistry, vol. 276, No. 11, pp. 8213–8218.*

Hatanake et al, "Transgenic plants of coffee *Coffea canephora* from embryogenic callus via *Agrobacterium tumefaciens*–mediated transformation", 1999, vol. 19, pp. 106–110.*

Kato M., et al., "Caffeine synthase gene from tea leaves," 406 Nature pp. 956–957 (2000).

Mazzafera P., et al., "S–Adenosyl–L–Methionine: Theobromine 1–N–Methyltransferase, and Enzyme Catalysing The Synthesis of Caffeine in Coffee," 37(6) Phytochemistry pp 1577–1584 (1994).

Kato, Misako, et al., "Purification and characterization of caffeine synthase from tea leaves," 120(2) Plant Physiology pp 579–586 (1999).

Suzuki, T., et al., "Biosynthesis of Caffeine by Tea–Leaf Extracts," 146 Biochemical Journal pp 87–96 (1975).

Ogawa, M., et al., "7–Methylxanthine Methyltransferase of Coffee Plants," 276(11) The Journal of Biological Chemistry pp 8213–8218 (2001).

Ashihara, H., et al., "Caffeine: a well known but little mentioned compound in plant science," 6(9) Trends in Plant Science pp 407–413 (2001).

Kato, Misako, et al., "Caffeine synthase gene from tea leaves," 406 Nature 956–957 (2000).

* cited by examiner

*Primary Examiner*—Ashwin Mehta
(74) *Attorney, Agent, or Firm*—Burns, Doane, Swecker & Mathis, LLP

(57) ABSTRACT

A theobromine gene derived from *Coffea arabica* and the polypeptide it encodes are disclosed. The disclosed polypeptide catalyzes biosynthesis of theobromine using 7-methylxanthine as the substrate. Also disclosed are plants transformed with the theobromine gene as to increase or inhibit biosynthesis of theobromine, methods of producing such plants, and seeds obtained from such plants. Caffeineless coffee may be obtained from the disclosed plants, as theobromine synthase participates in the biosynthesis of caffeine.

17 Claims, 9 Drawing Sheets

```
GTCCTGCATA TGAATGGAGC TCCAAGAAGT CCTGCATATG AATGGAGGCG AAGGCGAAGC AAGCTACGCC AAGAATTCAT CCTTCAATCA    90
ACTGGTTCTC GCCAAGGTGA AACCTGTCCT TGAACAATGC GTACGGGAAT TGTTGCGGGC CAACTTGCCC AACATCAACA AGTGCATTAA   180
AGTTGCAGAT TTGGGATGCG CTTCCGGACC AAACACACTT TTAACCGTTT GGGACACTGT ACAAAGTATT GACAAAGTTA AGCAAGAAAT   270
GAAGAATGAA TTAGAACGTC CCACCATTCA GGTTTTTCTG ACTGATCTTT TCCAAAATGA TTTCAATTCG GTTTTCATGC TGCTGCCAAG   360
CTTCTACCGC AAACTTGAGA AGAAAAATGG ACGCAAAATA GGATCGTGCC TAATAGCCGG AATGCCTGGC TCTTTCCACG GCAGACTCTT   450
CCCGAGGAG TCCATGCATT TTTACACTC TTCTTACAGT CTTCAGTTTT CCCAGCGGT TTGGTGACTG AATTGGGGAT   540
CACTGCGAAC AAAAGGAGCA TTTACTCTTC CAAAGCAAGT CCTCCGCCCG TCCAGAAGGC ATATTGGAT CAATTACGA AAGATTTTAC   630
CACATTTTTA AGGATGCGTT CGGAAGAGTT GCTTTCACGT GCCTTACTTG CATTTGTAAA GGAGATGAAT GCGACGGCCC   720
GAATACCATG GACTTACTTG AGATGGCAAT AAACGACTTG GTTGCTGAGG GACGTCTGGG GGAAGAAAAA TTGGACAGTT TCAATGTTCC   810
AATCTATACA GCTTCAGTAG AAGAAGTAAA GTGCATGGTT GAGGAGGAAG GTTCTTTTGA AATTTTATAC TTGCAGACTT TTAAGCTCCG   900
TTATGATGCT GGCTTCTCTA TTGATGATGA TTGCCAAGTA CAGCGATATA CCCCAGTATA CAGCTAGAG CAGGCCATGT   990
GGCATCATTA ATTAGATCAG TTACGAACC CATCCTAGCA AGTCATTTG GAGAAGCTAT TATACCTGAC ATATTCCACA GGTTTGCGAC   1080
GAATGCAGCA AAGGTTATCC GCTTGGGCAA AGGCTTCTAT AATAATCTTA TCATTTCTCT TGCCAAAAAA CCAGAGAAGT CAGACATATA   1170
AAAGCTTGTT TTTTAGTTGT TTTGTGTTA TGGGTTGTTT TCTGATACGG GGAAAGGATT CAGTGCGGTT GGGTTCTAT CCGAGTATTG   1260
TACTTTTTAT ATTATTAGTT GGTGTATAAT TATTATGTTA CATTGTTATA TTCGTAATAA AAGTGACGTA CAAAAATAAA ATATTTTCAT   1350
AAAAAAAAAA                                                                                         1360
```

FIG. 2A

```
TTTAGCAGTC CCAATTCGAT TTATGTACAA GTCCTGCATA TGAATGGAGC TCCAAGAAGT CCTGCATATG AATGGAGGCG AAGGCGATGC    90
AAGCTACGCC AAGAATTCAT CCTTCAATCA ACTGGTTCTC AGTTGCATTA GCCAAGGTGA AACCTGTCCT TGAACAATGC GTAGGGAAT  TGTTGCGGGC   180
CAACTTGCCC AACATCAACA AGTGCATTAA GTTGCGGAT  TTGGGATGCG CTTCCGGACC AAACACACTT TAACAGTTC  GGGACATTGT   270
ACAAGTATT  GACAAAGTTA GGCAAGAAAT GAAGAATGAA TTAGAACGTC CCACCATTCA GGTTTTTCTG ACTGATCTTT TCCAAAATGA   360
TTTCAATTCG GTTTTCATGT TGCTGCCAAG TTTCTACCGC AAACTTGAGA ACGCAAGATA GGATCGTGCC TAATAGCCGC   450
AATGCCTGGC TCTTTCCACG GCAGACTCTT CCCCGAGGAG TCAATGCATT TTTTACACTC CTTCAATTTT TATCCCAGGT   540
TCCCAGCGGT TTGGTGACTG AATTGGGGAT CACTGCGAAC AAAAGGAGCA TTTACTCTTC CAAAGCAAGT CCTCCGCCCG TCCAGAAGGC   630
ATATTTGGAT CAATTACGA  AAGATTTTA  AGGATTCGTT CGGAAGAGTT GCTTTCACGC GCCGAATGC  TCCTTACTTG   720
CATTTGCAAA GGAGATGAAT TCGACGGCCC GAATACCATG GACTTACTTG AGATGGCAAT AAACGACTTG GTTGTTGAGG GACATCTGGA   810
GGAAGAAAAA TTGGACAGTT TCAATGTTCC AATCTATGCA GCTTCAGTAG AAGAATTAAA GTGCATAGTT GAGGAGAAG  GTTCTTTTGA   900
AATTTTGTAC TTGGAGACTT TTAAGCTCCG TTATGATGCT GGCTTCTCTA TTGATGATGA TTGCCAAGTA AGATCCCATT CCCAGAATA    990
CAGCGATGAA CATGCTAGAG CAGGCCATGT GGCATCATTA CTTAGATCAG TTTACGAACC CATCCTCGCA AGATCATTTG GAGAAGCTAT  1080
TATACCTGAC ATATTCCACA GGTTTGCGAC GAATGCAGCA AGGTTATCC  GCTTGGGCAA AGGCTTCTAT AATAATCTTA TCATTTCTCT  1170
TGCCAAAAAA CCAGAGAAGT CAGACATATA AAAGCTTGTT TATAGTTGGT TTTTGTGCTA TGGTTTGTTT TCTGATACGG GGAAAGGATT  1260
TAGTGCGGTT GGGGTTCAAA AAAAAAAAA  AAAAAAAAAA AAAA                                                   1304
```

FIG. 2B

```
CTTTGGCAGT CCCAATTTGA TTTATGTACA AGTCCTGCAT ATGAATGGAG CTCCAAGAAG TCCTGCGGAT GAATGGAGGC GAAGGCGATA   90
CAAGCTACGC CAAGAATTCA GCCTACAATC AACTGGTTCT CGCCAAGGTG AAACCTGTCC TTGAACAATG CGTACGGAA  TTGTTGCGGG  180
CCAACTTGCC CAACATCAAC AAGTGCATTA AAGTTGCGGA TTTGGATGC  GCTTCTGGAC CAAACACACT TTTAACAGTT CGGGACATTG  270
TCCAAAGTAT TGACAAAGTT GGCCAGGAAA AGAAGAATGA ATTAGAACGT CCCACCATTC AGATTTTTCT GAATGATCTT TTCCCAAATG  360
ATTTCAATTC GGTTTTCAAG TGCTGCCAA  GCTTCTACG  CAAACTTGAG AAAGAAAATG GACGCAAAAT AGGATCGTGC CTAATAGGGG  450
CAATGCCCGG CTCTTTCTAC AGCAGACTGT TCCCGAGGA  GTCCATGCAT TTTTTACACT CTTGTTACTG TCTTCAATGG TTATCTCAGG  540
TTCCTAGCGG TTTGGTGACT GAATTGGGGA TCAGTACGAA CAAAGGGAGC AGGATTCTT  CCAAAGCAAG TCGTCTGCCC GTCCAGAAGG  630
CATATTTGGA TCAATTTACG AAAGATTTTA CCACATTTCT AGGATTGCCAT AGACTTACTT TGTTTTCACA TGGCCGAATG CTCCTTACTT  720
GCATTGTAA  AGGAGTTGAA TTAGACGCCC GGAATGCCCC CAGTCTATAT TCGGAAGAGT GAGATGGCAA TAAACGACTT GGTTGTGAG  GGACATCTGG  810
AGGAGAAAA  ATTGGATAGT TTCAATCTTC CAGTCTATAT AGTGCATAGT GAAGAAGTAA AGTGCATAGT AGCAGAGTAT GTTCATCTTT  900
AAATTTTATA CCTGGAGACT TTTAAGGTCC TTTACGATGC TGGCTTCTCT ATTGACGATG AACATATTAA ACATATTCCA AGCAGAGTAT GTTGCATCTT  990
CCGTTAGAGC AGTTACGAA  CCCATCCTCG CAAGTCATTT TGGAGAAGCT ATTATACCTG ATTATATTCCA AGCAGAGAA  CAGGTTTGCG AAGCATGCAG 1080
CAAAGGTTCT CCCCTTGGGC AAAGGCTTCT ATAATAATCT TATCATTTCT CTCGCCAAAA AGCCAGAGAA GTCAGACGTG TAAAAGTTTG 1170
TTTTTGTGTT GGGAAAGGA ATAAGTGCCG TTGGGGTCT  TTCGGGTATT GTGCTTTTA  TATTATATTG TTTTGTATCC GTAATAAAAG 1260
TGGTGTGTAA GAATAAGATA TTTGACATAT ATTATTTCA  AAAAAAAAA  AAAAAA                                     1316
```

FIG. 2C

```
AGCAGTCGCA ATTCGATTGT CCTGCATATG AATGGAGCTC CAAGAAGTCC TGCATATGAA TGAAGGTGAA GGCGATACAA GCTACGCCAA    90
GAATGCATCC TACAATCTGG CTCTTGCCAA GGTGAAACCT GGTGAAACCT TTCCTTGAAC AATGCATACG AGAATTGTTG CGGGCCAACT TGCCCAACAT   180
CAACAAGTGC ATTAAAGTTG CGGATTTGGG ATGCGCTTCT GGACCAAACA CACTTTTAAC AGTGCGGGAC ATTGTGCAAA GTATTGACAA   270
AGTTGGCCAG GAAGAGAAGA ATGAATTAGA ACGTCCCACC ATTCAGATTT TTCTGAATGA TCTTTTCCAA AATGATTTCA ATTCGGTTTT   360
CAAGTTGCTG CCAAGCTTCT ACCGCAAACT CGAGAAGAA ATGGACGCA ACACTCTTGT ACAGTGTTCA GTGCCTAATA AGCGCAATGC CTGGCTCTTT   450
CTACGGCAGA CTCTTCCCG AGGAGTCCAT GCATTTTG CACTCTTGTT ACAGTGTTCA TTGGTTATCT CAGGTTCCCA GCGGTTTGGT   540
GATTGAATTG GGGATTGGTG CAAACAAAGG GAGTATTTAC TCTTCCAAAG GATGTCGTCC GCCCGTCCAG AAGGCATATT TGGATCAATT   630
TACGAAAGAT TTTACCACAT TTCTAAGGAT TCATTCGAAA GAGTTGTTTT CACGTGGCCG AATGCTCCTT ACCTGCATTT GTAAAGTAGA   720
TGAATTCGAC GAACCGAATC CCCTAGACTT TTACACCTTC GCAATAAACG ACTTGATTGT TGAGGGACTT CTGGAGGAAG AAAAATTGGA   810
TAGTTTCAAT ATTCCATTCT TTACACCTTC AGCAGAAGAA GTAAAGTGCA TAGTTGAGGA GGAAGGTTCT TGCGAAATTT TATATCTGGA   900
GACTTTTAAG GCCCATTATG ATGCTGCCTT CTCTATTGAT CAGTAAGATC ECATGAACAA ATTAAAGCAG AGTATGTGGC   990
ATCATTAATT AGATCAGTTT ACGAACCAT CCTGCAAGT AAGCTATTAT GCCTGACTTA TTCCACAGGC TTGCGAAGCA  1080
TGCAGCAAAG GTTCTCCACA TGGGCAAAGG CTGCTATAAT AATCTTATCA TTTCTCTGC CAAAAGCCA GAGAAGTCAG AGTGTAAAA  1170
GTTTGTTTT AGTTGGTTT TGTGCCGTTG GGGTCTTTC GTTTGTATT CGTAATAAAA GTGATGTGCA AGAATAAGAT  1260
ATTTAGTACA ATATTTCAT AAAAAAAAAA AAAAAAAA                                                         1298
```

FIG. 2D

```
MXMT1   MELQEVLHMNEGEGDTSYAKNASYN-LALAKVKPFLEQCIRELLRANLPN     49
MTL1    ::::::::::G:::EA:::::S:F:Q:V::::::V::::V:::::::::       50
MTL2    ::::::::::G::::A:::::S:F:Q:V::::::V::::VG::::::::       50
MTL3    ::::::::R::G::::::::::SA::Q:V::::::V::::V::::::::       50

MXMT1   INKCIKVADLGCASGPNTLLTVRDIVQSIDKVGQEEKNELERPTIQIFLN      99
MTL1    ::::::::::::::::::::::W:T::::::K::M:::::::::V::T       100
MTL2    ::::::::::::::::::::::::::::::R::M:::::::::V::T        100
MTL3    ::::::::::::::::::::::::::::::K::::::::::::::::        100

MXMT1   DLFQNDFNSVFKLLPSFYRKLEKENGRKIGSCLISAMPGSFYGRLFPEES      149
MTL1    ::::::::::M:::::::::::::::::::::::A::::H:::::::::       150
MTL2    ::::::::::M:::::::::::::::::::::::A:::::H::::::::       150
MTL3    :::P:::::::::::::::::::::::::::::::::::S:::::::::       150

MXMT1   MHFLHSCYSVHWLSQVPSGLVIELGIGANKGSTYSSKGCRPPVQKAYLDQ      199
MTL1    ::::::S::LQF:::::::::T::::T:::R::::::ASP::::::::::      200
MTL2    ::::::S::LQF:::::::::T::::T::R:::::ASP::::::::::       200
MTL3    ::::::CLQ:::::::::::T::::ST:::::::::AS:L::::::::       200

MXMT1   FTKDFTTFLRIHSKELFSRGRMLLTCICKVDEFDEPNPLDLLDMAINDLI      249
MTL1    ::::::::::MR:E::L:::::::::::::G::C:G::TM:::E:::::V      250
MTL2    :::::::::R:E::L:::::::::::::G::::G::TM:::E:::::V       250
MTL3    :::::::::E::::H::::::::::GE:L:AR:AI:::E::::::V         250

MXMT1   VEGLLEEEKLDSFNIPFFTPSAEEVKCIVEEEGSCEILYLETFKAHYDAA      299
MTL1    A::R:G:::::::::V:IY:A:V::::M:::::F:::::Q:::LR:::G       300
MTL2    :::H:::::::::V:IYAA:V::L:::::::F::::::::LR:::G         300
MTL3    :::H:::::::L:VYI::::::::::::::F:::::::::VL:::G         300

MXMT1   FSIDDDYPVRSH------EQIKAEYVASLIRSVYEPILASHFGEAIMPDL      343
MTL1    ::::::CQ::::SPVYSD:HAR:AH:::::::::::::::::::I::I        350
MTL2    ::::::CQ::::SPEYSD:HAR:AH::::L:::::::::N:::::I::I       350
MTL3    :::::EH------::::::::SV:A:::::::::::::::::I::I         337

MXMT1   FHRLAKHAAKVLHMGKGCYNNLIISLAKKPEKSDV    378
MTL1    :::F:TN::::IRL:::F::::::::::::::::I    385
MTL2    :::F:TN::::IRL:::F::::::::::::::::I    385
MTL3    :::F:::::::PL:::F:::::::::::::::::     372
```

FIG. 3

THEOBROMINE SYNTHASE POLYPEPTIDE OF COFFEE PLANT AND THE GENE ENCODING SAID POLYPEPTIDE

BACKGROUND OF THE INVENTION

1. Field of the Invention

This invention relates to theobromine synthase polypeptide and the gene encoding said enzyme.

2. Prior Art

Coffee is a drink consumed all over the world with favorite and its utility is markedly large. On the other hand, it is known that excessive ingestion of caffeine, which is contained in coffee, causes harmful effects. Caffeine is one of xanthine derivatives and theophylline and theobromine are also the members of the xanthine derivatives. These xanthine derivatives are known to inhibit phosphodiesterase, thereby the amount of cAMP is increased. As the result, xanthine derivatives exhibit excitatory effect on the central nerves system and enhance function of the circulatory system. When they are ingested at a suitable amount, such effects of xanthine derivatives are useful for spiritual elevation. However, when the amount of digestion is excessive, they would cause harmful effects as mentioned above. Therefore, there has been a strong demand on production of a caffeine-less coffee all over the world.

To obtain caffeine-less coffee, attempts to obtain a gene involved in biosynthesis of xanthine derivatives have been performed, in the purpose to achieve artificial control of biosynthesis of caffeine. In FIG. 1 (cited from Advances in Botanical Research, Vol. 30, Academic Press (1999) p149), the pathway working for caffeine biosynthesis in coffee plants is shown. In FIG. 1, the arrow with solid line indicates the main pathway of caffeine synthesis and the arrow with dotted line indicates the minor pathway of caffeine synthesis, respectively. As shown in the second line of FIG. 1, the pathway operating for biosynthesis of caffeine from xanthosine via 7-methylxanthine and theobromine has been known, which is the main pathway for biosynthesis of caffeine biosynthesis in coffee plants. The latter half of the main biosynthesis pathway of caffeine is composed of three steps of N-methylation reactions. These N-methylation reactions have been known to be dependent on S-adenosylmethoinine. There also exists a pathway (third line in FIG. 1) in which caffeine is biosynthesized from 7-methylxanthine via para-xanthine, but it is known that contribution of this pathway is not significant. With regard to the first methylation reaction to synthesize 7-methylxanthine, a gene encoding an enzyme responsible for said reaction has been obtained and it has been already reported (International Laid-Open Publication No. WO 97/35960). However, genes involved in the second step methylation reaction and the third step methylation reaction have not been known yet. For effective and accurate manipulation of caffeine biosynthesis, more knowledge on genes that encode enzymes involved in caffeine biosynthesis should be obtained.

SUMMARY OF THE INVENTION

The first aspect of this invention is a polypeptide consisting of an amino acid sequence defined by amino acid numbers from 1 to 378 shown in SEQ ID NO: 1 in a Sequence List. A polypeptide consisting of an amino acid sequence exhibiting at least 90% of homology with SEQ ID NO: 1 is also within the scope of this invention, so far as the polypeptide has the activity to biosynthesize theobromine using 7-methylxanthine as the substrate. Such sequence may be obtained by making deletions, insertions, substitutions or any combinations thereof in the amino acid sequence of SEQ ID NO: 1.

The second aspect of this invention is a gene consisting of a base sequence defined by base numbers from 1 to 1298 shown in SEQ ID NO: 2 in a Sequence List. A gene that hybridizes with SEQ ID NO: 2 under a stringent confdition and a gene consisting of a base sequence exhibiting at least 90% of homology with SEQ ID NO: 2 is also within the scope of this invention, so far as the gene encodes a polypeptide having the activity to biosynthesize theobromine using 7-methylxanthine as the substrate. Such sequence may be obtained by making deletions, insertions, substitutions or any combinations thereof in the base sequence of SEQ ID NO: 2.

The third aspect of this invention is a transformed plant wherein expression of said gene is inhibited in the plant to decrease biosynthesis of theobromine and a seed obtained from the transformed plant. Preferably, the plant to be transformed is selected from the group consisting of *Coffea arabica, Coffea canephora, Coffea liberica* and *Coffea dewevrei*.

The fourth aspect of this invention is a transformed plant wherein said gene is introduced in the plant to increase biosynthesis of theobromine and a seed obtained from the transformed plant. Preferably, the plant to be transformed is selected from the group consisting of *Coffea arabica, Coffea canephora, Coffea liberica* and *Coffea dewevrei*.

BRIEF DESCRIPTION OF THE DRAWINGS

The present invention will be further explained in detail hereafter with reference to the accompanying drawings, in which:

FIG. 2 is a drawing showing base sequences of cDNAs obtained from MTL1, MTL2, MTL3 and MXMT1. FIG. 2A shows the base sequence of cDNA obtained on clone #1 (SEQ ID NO: 4). FIG. 2B shows the base sequence of cDNA obtained on clone #6 (SEQ ID NO: 6). FIG. 2C shows the base sequence of cDNA obtained on clone #35 (SEQ ID NO: 8). FIG. 2D shows the base sequence of cDNA obtained on clone #45 (SEQ ID NO: 2);

FIG. 3 is a drawing showing alignment of amino acid sequences obtained from MXMT1 (SEQ ID NO: 2), MTL1 (SEQ ID NO: 4), MTL2 (SEQ ID NO: 6) and MTL3 (SEQ ID NO: 8);

DETAILED DESCRIPTION OF THE INVENTION

Figure 1:
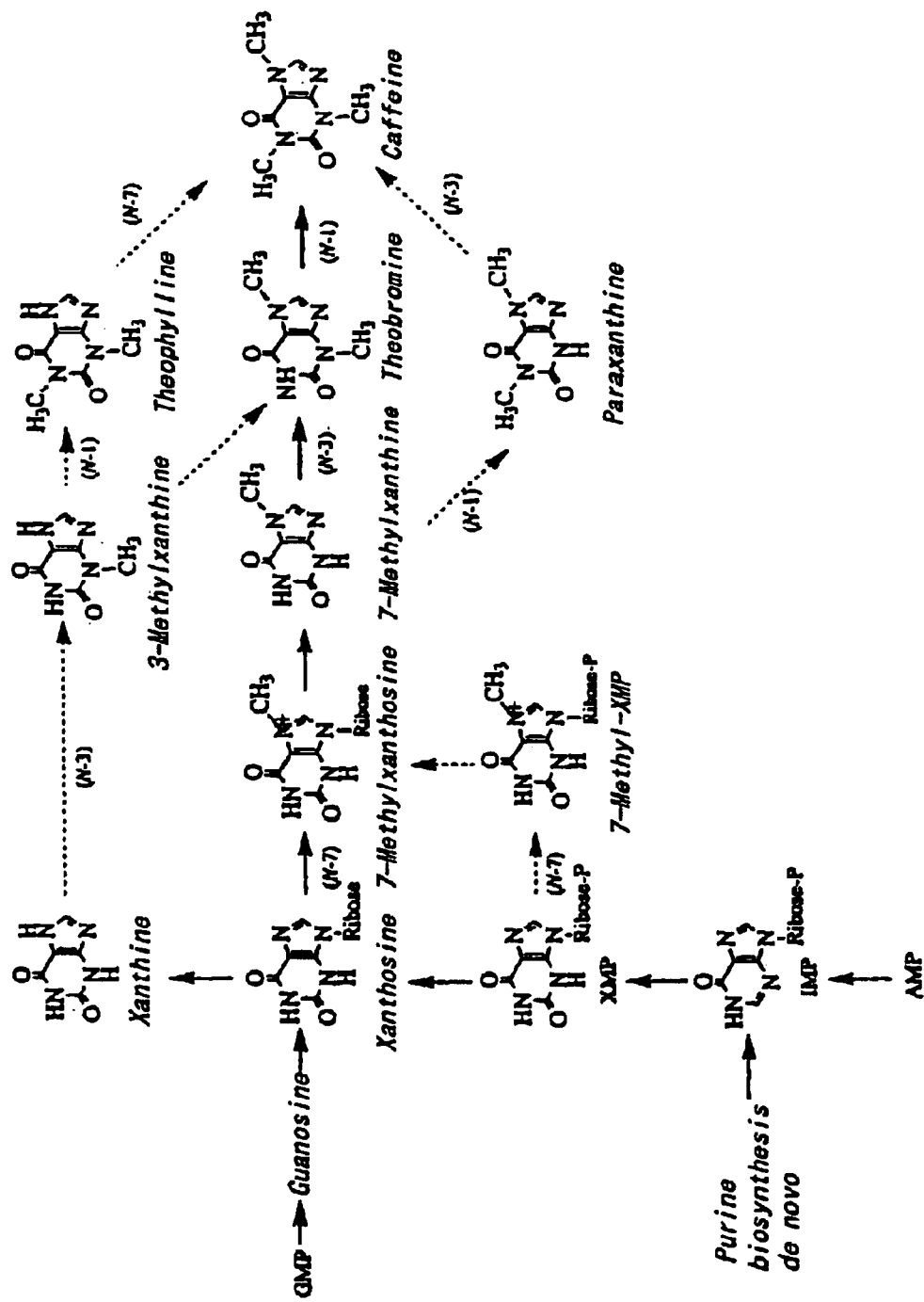
FIG. 1 is a drawing showing the pathway of caffeine biosynthesis.

The present inventors remarked an enzyme participating to the second methylation step reaction and responsible for biosynthesis of theobromine, and they have obtained the gene encoding the enzyme. The enzyme is an enzyme operating to catalyze biosynthesis of theobromine from 7-methylxanthine. Therefore, when expression of the gene encoding said enzyme in inhibited, it would result in decrease of theobromine biosynthesis. In the pathway of caffeine biosynthesis, caffeine is synthesized through N-methylation of theobromine. Then when biosynthesis of theobromine is inhibited, biosynthesis of caffeine would be inhibited as well. As described above, theobromine and caffeine exhibit similar pharmacological effect as xanthine derivatives. Therefore, isolation of a gene encoding an enzyme, which enables concurrent manipulation of theobromine biosynthesis and caffeine biosyntheses, has a great significance. That is, if a gene encoding an enzyme responsible for the final step of caffeine biosynthesis, i.e. the third methylation step, is isolated, then expression of the gene can be inhibited. As a result, biosynthesis of caffeine would be reduced, but biosynthesis of theobromine would not be reduced. Moreover, accumulation of theobromine is expected to occur, as the metabolism of theobromine is inhibited. Thus, considering that pharmacological effect of theobromine is similar to that of caffeine, the effect of the present invention, which relates to isolation of a gene encoding theobromine synthase, can be estimated to be significant.

The present invention relates to theobromine synthase gene derived from *Coffea arabica*, consisting of a base sequence defined by the base numbers 1 to 1298 shown in SEQ.ID. NO: 2 in a Sequence List. As described above, in coffee plants, theobromine synthase catalyzes methylation reaction at biosynthesis of theobromine using 7-methylxanthine as the substrate. The gene defined by the base sequence described in SEQ.ID. NO: 2 in a Sequence List is a gene encoding theobromine synthase having such characteristic.

According to technique of gene recombination, artificial modification can be achieved at a specific site of basic DNA, without alteration or with improvement of basic characteristic of said DNA. Concerning a gene having native sequence provided according to this invention or modified sequence different from said native sequence, it is also possible to perform artificial modification such as insertion, deletion or substitution to obtain gene of equivalent or improved characteristic compared with said native gene. Moreover, a gene with such mutation is also included in the range of this invention. That is, the gene, consisting of a base sequence hybridizes with said base sequence shown in SEQ ID NO: 2 in the sequence list under stringent condition, means a gene in which 10 or less, preferably 7 or less, and more preferably 3 or less bases of the sequence is deleted, substituted or added to the base sequence shown in SEQ ID NO: 2 in a Sequence List. Moreover, such gene exhibits homology 90% or more, preferably 95% or more and still preferably 99% or more with the base sequence shown in SEQ ID NO: 2 in a Sequence List. In addition, such gene hybridizes with the base sequence shown in the SEQ ID NO: 2 in a Sequence List under stringent condition. Such gene is also within the range of this invention so far as it encodes a polypeptide having the characteristic as theobromine synthase, that catalyzes biosynthesis of theobromine using 7-methylxanthine as the substrate.

Furthermore, this invention relates to polypeptide of theobromine synthase derived *Coffea arabica*, consisting of an amino acid sequence defined by the amino acid numbers from 1 to 378 shown in SEQ ID NO: 1 in a Sequence List. The polypeptide consisting of an amino acid sequence in which a part of said polypeptide defined by amino acid sequence shown in SEQ ID NO: 1 is deleted, substituted or added with another amino acid sequence means a polypeptide in which 10 or less, preferably 7 or less, and more preferably 3 or less amino acids of the sequence is deleted, substituted or added to the amino acid sequence shown in SEQ ID NO: 1 in a Sequence List. Moreover, such polypeptide exhibits homology 90% or more, preferably 95% or more and still preferably 99% or more with the amino acid sequence shown in SEQ ID NO: 1 in a Sequence List. Such polypeptide is also within the range of this invention so far as it exhibits characteristic as theobromine synthase, that catalyzes biosynthesis of theobromine using 7-methylxanthine as the substrate. Incidentally, the polypeptides shown in SEQ.ID. NO: 3, SEQ.ID. NO: 5 and SEQ.ID. NO: 7 in a Sequence List can be obtained from coffee arabica (Coffea arabica), and the polypeptides have higher than 80% of homology compared with the amino acid sequence of SEQ.ID. NO: 1 in a Sequence List. These three polypeptides did not exhibit activity as theobromine synthase, despite of high homology to SEQ.ID. NO: 1 in a Sequence List.

A transformed plant, in which expression of theobromine synthetase gene described in SEQ.ID. NO: 2 in a Sequence List is inhibited to decrease biosynthesis of theobromine, is also within the scope of the present invention. The theobromine synthase gene of the present invention is, as mentioned above, a gene encoding an enzyme involved in biosynthesis of theobromine in coffea arabica. Thus, by inhibiting expression of the gene according to the present invention, biosynthesis of theobromine is assumed to decrease in a plant, whereby it enables decrease of theobromine content and caffeine content in the plant. As a plant of the target in which expression of theobromine synthase gene of the present invention is inhibited, coffee plants such as *Coffea arabica, Coffea canephora, Coffea liberica* and *Coffea dewevrei* and the like can be exemplified.

In these plants, by inhibiting expression of the gene of the present invention, biosyntheses of theobromine and caffeine would be reduced. As a means for inhibiting expression of the gene of the present invention, a method utilizing an antisense gene (antisense gene method) can be adopted. The antisense gene means a gene that expresses a base sequence complementary to mRNA, a transcription product of DNA constituting a certain gene. The transcription product of the antisense gene is complementary to an inherent mRNA, then the antisense gene can inhibit gene expression at the stage of translation. By utilizing this technique, expression of theobromine synthase gene can be inhibited.

In addition, other methods that can inhibit expression of a gene have been known. By destruction of a targeted gene, expression of the gene can be inhibited. Moreover, in a plant, technique of co-suppression (transwitch technique) has been known. According to the technique, expression of the targeted gene can be inhibited by phenomenon of gene interference, even when sense gene is introduced and overexpressed. Moreover, it has been reported in recent years that Double-stranded RNA interference (RNAi) method using a double stranded RNA is effective to inhibit expression of a gene (Chiou-Fen Chuang et al. PNAS (2000) vol. 97, 4985–4990). It has been demonstrated that a double strand RNA can inhibit expression of a gene in a sequence specific manner, according to the research mainly utilizing nematodes (C.elegans) or fruit fly. In the RNAi method, such double strand RNA is utilized and it has been recently demonstrated that the method is effective for not only nematodes or fruit fly but also for plants such as *Arabidopsis thaliana* Heynh. The mechanism involved in inhibition of gene expression by the RNAi method is not known yet.

However, this method would enable inhibition of expression of a gene, with higher efficiency compared with the above-mentioned antisense method.

By the way, purine alkaloids such as caffeine and theobromine, can exhibit effect to avoid insects and the effect is considered to be the existence value of purine alkaloids in a plant. Thus, the gene of the present invention can be introduced in a plant and biosythesis of theobromine can be increased in the plant, whereby the plant body would exhibit insect-avoiding activity. As described above, the enzyme of the present invention is responsible for biosynthesis of theobromine using 7-methylxantine as the substrate. Therefore, it is assumed that, when the above-mentioned gene encoding the 7-methylxanthine synthase (International Laid-Open Publication WO 97/35960) and the gene of the present invention are introduced into a plant concurrently, the effect would be particularly significant. When the activity of 7-methylxanthine synthase is enhanced, the amount of substrate available for the enzyme according to the present invention would be increased. As a result, accumulation of theobromine, which is the objective product, is expected to occur.

As a method to produce a transformant, a method generally well known in this art can be adopted. A vector available for the present invention may include plasmid vectors, for example pBI121 can be exemplified, but the scope the vector is not to be limited to them. Such vector can be introduced into, for example, Agrobacterium. Then the bacteria can be utilized for infection of callus or plantlets, resulting in production of transformed plants. Furthermore, it is possible to obtain seeds derived from such transformed plants. In Japanese Laid-Open Patent Application No. 2000-245485, the present inventors have reported a method comprising infection of an embryogenic callus of a coffee plant by *Agrobacterium tumefaciens* EHA101 and the method enables transformation of coffee plants with high efficacy. The method for transformation described in Japanese Laid-Open Patent Application No. 2000-245485 is assumed to be particularly useful.

EXAMPLES (Amplification by PCR)

A pair of degenerate oligonucleotide (Forward primer, GGITGYDSIDSIGGICCIAAYAC (SEQ ID NO: 9); Reverse primer, ARIYKIYYRTRRAAISWICCIGG (SEQ ID NO: 10)) was synthesized, based on the region conserved among TCS1 (Kato et al., 2000, GenBank accession no. AB031280) aid two proteins (Z99708 and AC008153), with their functions unknown, of *Arabidopsis thaliana*. These oligonucleotides correspond to amino acid sequences of GC(A/S)(A/S)GPNT (SEQ ID NOs: 11–14) and PGSF(H/Y)(G/K)(R/N)LF (SEQ ID NOs: 15–22), respectively. In a 25 µl of reaction mixture containing *Coffea arabica* cDNA and the above-mentioned primer pair, PCR was performed under the conditions described below. That is, after reaction at 94° C. for one minute, 30 cycles of denaturation at 94° C. for 30 seconds, annealing at 52° C. for 30 seconds and extension at 72° C. for one minutes was performed, which was followed by a final extension at 72° C. for 7 minutes, whereby the PCR reaction was completed. The amplified cDNA fragment of about 270 base pairs was used for screening of cDNA library.

(cDNA Library Construction and Screening)

Total RNA was extracted from young leaves of coffee (*Coffea arabica*) and it was purified to mRNA by oligo-dT column (Pharmacia). cDNA was synthesized from mRNA using ZAPII CDNA synthesis kit (Stratagene), it was introduced into λZAPII vector to prepare phage library. Then CDNA library was screened using the above-mentioned amplified fragment as a probe. Thirty-five of resulting positive plaques were selected randomly and converted to plasmids, then physical mappping and partial sequencing were performed. As a result, they were clarified into 4 groups of independent clones.

Clones #1, #6, #35 and #45 were representatives of each group having the longest lengths close to full length cDNAs, and base sequences of the clones were determined. Moreover, the deduced amino acid sequences encoded by the open reading frame regions of the base sequences were determined. The base sequences determined by sequencing were shown in FIG. 2. The base sequence of cDNA obtained on the clone #45 was shown in SEQ.ID. NO: 2 in a Sequence List and in FIG. 2D. The region corresponding to open reading frame of said gene ranged from base numbers 32 to 1168, and the deduced amino acid sequence encoded by said region was shown in SEQ.ID. NO: 1 in a Sequence List. Moreover, the base sequence of cDNA obtained on the clone #1 was shown in SEQ.ID. NO: 4 in a Sequence List and in FIG. 2A. The region corresponding to open reading frame of said gene ranged from base numbers 14 to 1171, and the deduced amino acid sequence encoded by said region was shown in SEQ.ID. NO: 3 in a Sequence List. Furthermore, the base sequence of CDNA obtained on the clone #6 was shown in SEQ.ID. NO: 6 in a Sequence List and in FIG. 2B. The region corresponding to open reading frame of said gene ranged from base numbers 44 to 1201, and the deduced amino acid sequence encoded by said region was shown in SEQ.ID. NO: 5 in a Sequence List. Moreover, the base sequence of cDNA obtained on the clone #35 was shown in SEQ.ID. NO: 8 in a Sequence List and in FIG. 2C. The region corresponding to open reading frame of said gene ranged from base numbers 45 to 1163, and the deduced amino acid sequence encoded by said region was shown in SEQ.ID. NO: 7 in a Sequence List. In the following, the gene corresponds the clone #45 was designated to MXMT1, the clone #1 was designated to MTL1, the clone # 6 was designated to MTL2, and the clone #35 was designated to MTL3, respectively.

The alignment compared among amino acid sequences encoded by MXMT1, MTL1, MTL2 and MTL3 was shown in FIG. 3. As a result, it was shown that these four sequences exhibit extremely high homology. To confirm the functions charge by these polypeptides, genes corresponding to each clone were expressed in *E. coli* to confirm their enzymatic activities.

(Expression of GST fused protein)

Figure 4:
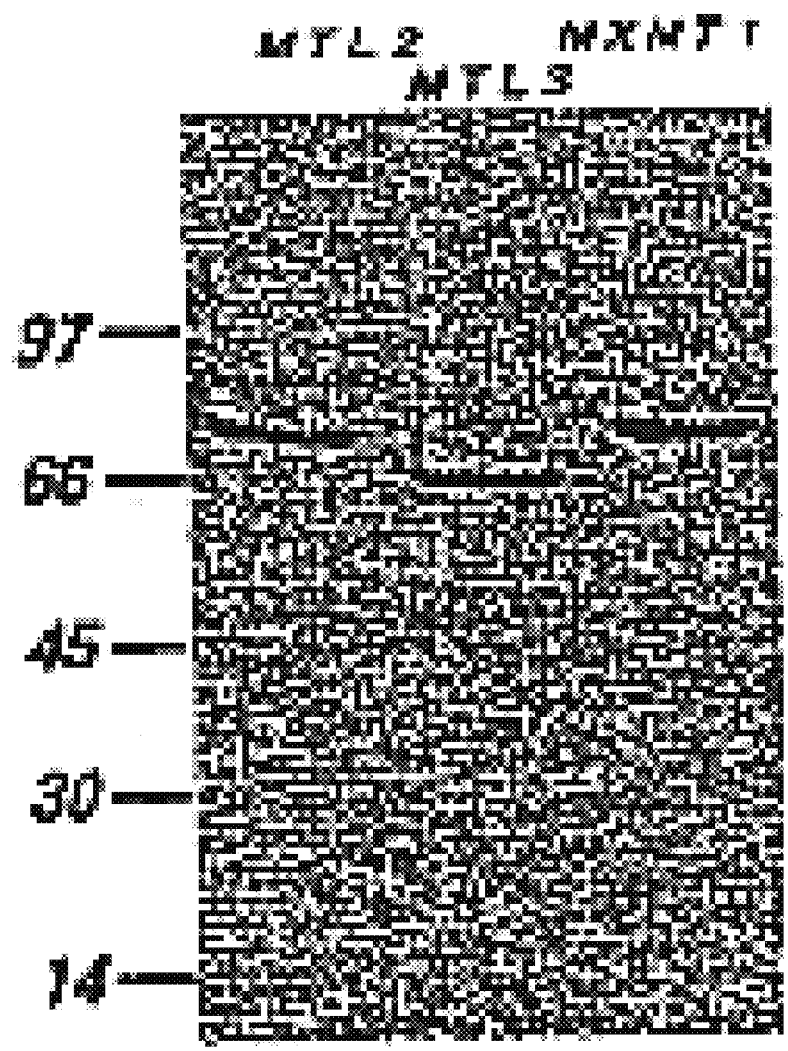
FIG. 4 is a photograph showing the results of SDS-PAGE analyses performed on fusion proteins obtained from MTL2, MTL3 and MXMT1.

The open reading frame regions of MTL1 (Clone #1), MTL2 (Clone #6), MTL3 (Clone #35) and MXMT1 (Clone #45) were amplified by PCR (polymerase chain reaction). Then, they were optionally cloned into pGEX 4T-2 vector (Pharmacia) and *E. coli* (JM109) cells were transformed with the resulting plasmids. The obtained *E. coli* cells were cultured in LB liquid medium containing ampicillin. When OD600 of the culture reached to 0.5, IPTG (isopropyl thio-β-D-galactoside) was added to it and the final concentration of IPTG was made to 1 mM, then the mixture was further cultured at 16° C. for 6 hours. *E. coli* was desrupted by a sonicator and the protein of the purpose was purified by glutathione Sepharose 4B as a GST (glutathione S-transferase) fusion protein. Concentration of the protein was measured by the Bradford method. Each of the GST fusion protein (500 ng) was separated by SDS-PAGE (sodium dodecyl sulfate polyacrylamide gel electrophoresis), then it was stained by CBB (coumasie Brilliant Blue) to confirm purification. The purities of the resulting GST fusion proteins were analyzed by SDS-PAGE and the results were shown in FIG. 4. In FIG. 4, lane 1 shows the result of MTL2 fusion protein, lane 2 shows the result of MTL3 fusion protein, lane 3 shows the result of MXMT1 fusion protein, respectively. As a result, the resulting three fusion proteins were shown to be approximately pure.

(Measurement of Enzymatic Activities by Thin Layer Chromatography)

Figure 5:
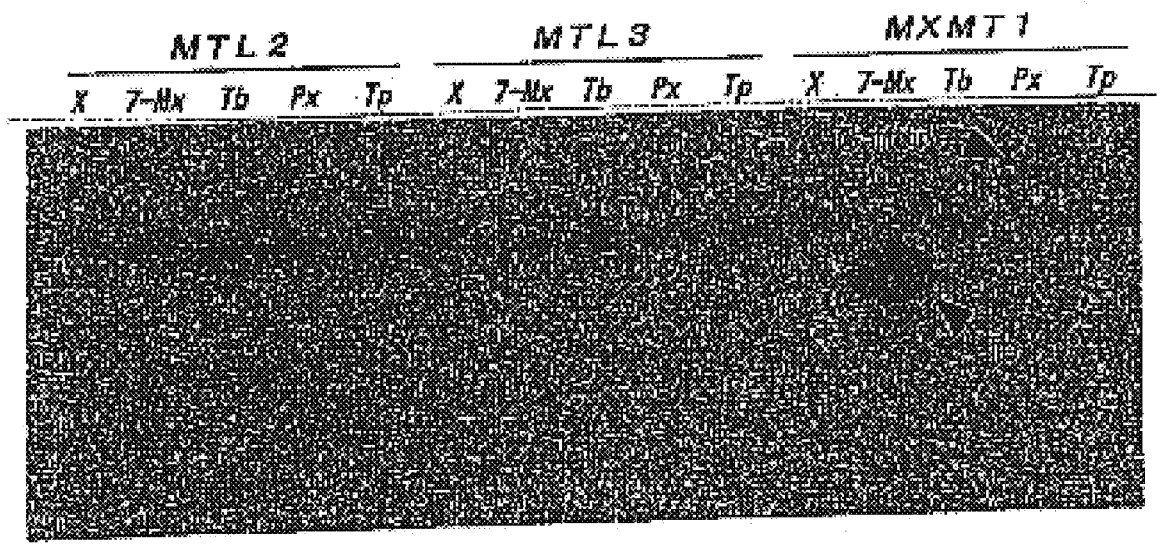
FIG. 5 is a photograph showing the results of TLC to analyze enzymatic activities of the fusion proteins obtained from MTL2, MTL3 and MXMT1.

Measurement of enzymatic activity was performed using thin layer chromatography (TLC), based on the method of Kato et al. (Plant Physiol., 1996, 98, 629–636). In concrete, the reaction mixture of 100 μl, containing 100 mM Tris-HCl (pH 7.5), 200 μM substrate (xanthine, 7-methylxanthine, theobromine, paraxanthine, theophylline), 4 μM $^{14}$C-labeled S-adenosylmethionine, 200 μM $MgCl_2$, 200 ng GST fusion protein, was incubated at 27° C. for 2 hours. After the reaction, the resulting mixture was extracted with 1 ml of chloroform, the chloroform layer was recovered, then chloroform was evaporated by speed back concentrator. The residue was dissolved in 5 μl of 50% methanol solution, then the solution was developed by TLC (solvent for development was water:acetic acid:n-butanol=2:1:4, v/v/v). After the development, signal of radio activity was detected by image analyzer (Fuji BAS 2000). The result of enzymatic activity, which was measured on the fusion proteins derived from MTL2, MTL3 and MXMT1 using xanthine (X), 7-methylxanthine (7-Mx), theobromine (Tb), paraxanthine (Px) and theophylline (Tp) as the substrate, was shown in FIG. 5. From FIG. 5, it was revealed that the fusion protein derived from MXMT1 exhibited potent activity to synthesize theobromine, using 7-methylxanthine as the substrate. The fusion protein derived from MXMT1 also exhibited activity to synthesize caffine, using paraxanthine as the substrate, but its relative activity was 15% of the above-mentioned activity. On the other hand, the fusion proteins derived from MTL2 and MTL3 did not exhibit activity as a methyl transferase, using the above-mentioned compounds as the substrate.

(Enzymatic Activity Measurement and Identification of the Product by HPLC)

Using high performance liquid chromatography (HPLC), enzymatic activity of the MXMT1 fusion protein was measured and reaction product obtained from the enzymatic reaction was identified. The reaction mixture of 100 μl, containing 100 mM Tris-HCl (pH 7.5), 200 μM of substrate (7-methylxanthine, paraxanthine, theobromine), 50 μM of S-adenosylmethionine, 200 μM of $MgCl_2$, 200 ng of GST fusion protein, was incubated at 27° C. for 2 hours. After incubation, the mixture was extracted with 1 ml of chloroform, the chloroform layer was recovered, then chloroform was evaporated by a speed back concentrator. The residue was dissolved in 50 μl of 12% acetonitrile. Then the solution was fractionated by HPLC (Shodex Rspak DS-613 column) provided with UV detection system. As the solution for development, 12% acetonitrile was used and the signal was detected for absorbance of 254 nm.

Figure 6:
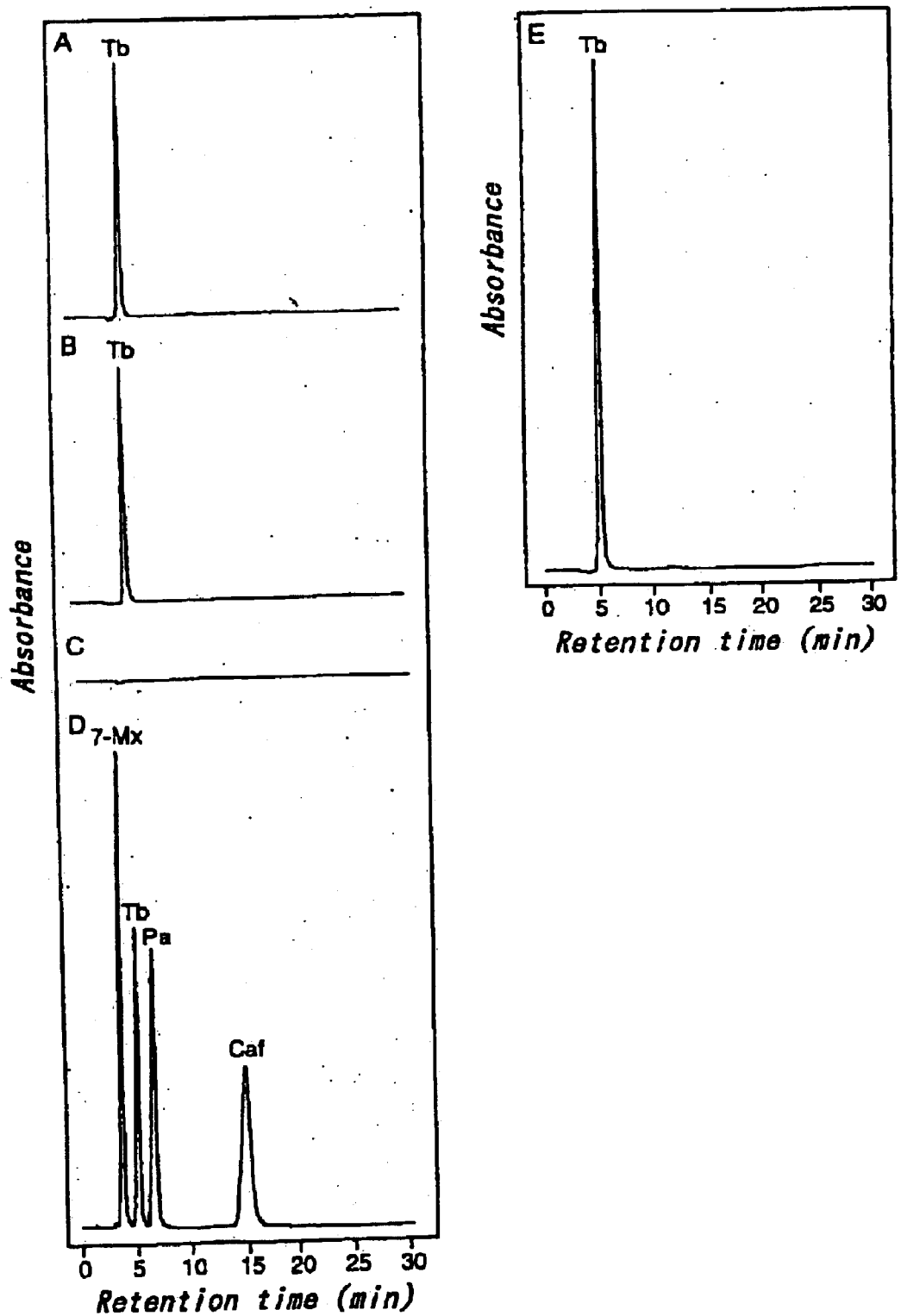
FIGS. 6A–6E shows results of HPLC performed to identify reaction products in the enzymatic reaction mixture of the fusion protein obtained from MXMT1 identified by HPLC.

The result was shown in FIG. 6. The MXMT1 fusion protein was reacted with S-adenosylmethionine and 7-methylxanthine, which is the substrate and the reaction product was analyzed by HPLC. The chart exhibiting the result was shown in FIG. 6A. Moreover, theobromine was analyzed for a standard compound using HPLC and the chart exhibiting the result was shown in FIG. 6B. For preparation of negative standard, the MXMT1 fusion protein, S-adenosylmethionine and 7-methylxanthine was mixed and the reaction was immediately stopped and the chart exhibiting the result was shown in FIG. 6C. For standard products, 7-methylxantine, theobromine, paraxanthine and caffeine were analyzed by HPLC, and the chart exhibiting the result was shown in FIG. 6D. Furthermore, S-adenosylmethionine and 7-methylxanthine was reacted with MXMT1 fusion protein and then theobromine was added to the reaction mixture. The chart exhibiting the result was shown in FIG. 6E. The peak position of the reaction product detected in FIG. 6A coincided with the position of theobromine, which was analyzed as the standard compound. In addition, when theobromine was added to the enzymatic reaction mixture, only one peak was observed. Therefore, it was shown that theobromine was formed by enzymatic reaction of the MXMT1 fusion protein, using 7-methylxantine as the substrate.

According to the present invention, the polypeptide of theobromine synthase derived from coffea arabica and the gene encoding said polypeptide were provided. As theobromine synthase participates in biosynthesis of caffeine, caffeineless coffee would be obtained by preparing a transformed plant, wherein expression of gene encoding said enzyme was inhibited.

What is claimed is:

1. An isolated nucleotide sequence encoding a polypeptide consisting of the amino acid sequence defined by amino acids 1–378 of SEQ ID NO:1.

2. An isolated nucleotide sequence encoding a polypeptide consisting of an amino acid sequence exhibiting at least 99% identity with the amino acid sequence defined by amino acids 1–378 of SEQ ID NO:1, wherein said polypeptide has the activity to biosynthesize theobromine using 7-methylxanthine as the substrate.

3. An isolated nucleotide sequence consisting of nucleotides 1–1298 of SEQ ID NO:2.

4. An isolated nucleotide sequence exhibiting at least 99% identity with the nucleotide sequence defined by nucleotides 1–1298 of SEQ ID NO:2, wherein said isolated nucleotide sequence encodes a polypeptide having the activity to biosynthesize theobromine using 7-methylxanthine as the substrate.

5. A method for decreasing theobromine synthesis in a plant, said method comprising introducing the nucleotide sequence of any one of claims 1–4 into a plant cell in antisense orientation, wherein expression of said nucleotide sequence in antisense orientation in said plant results in a decrease in theobromine synthesis.

6. A transformed plant produced using the method of claim 5.

7. The plain according to claim 6, wherein said plant is selected from the group consisting of *Coffea arabica, Correa canephora, Coffea liberica*, and *Coffea dewevrei*.

8. A seed obtained from the transformed plant according to claim 6, wherein said seed contains said nucleotide sequence in antisense orientation.

9. A seed obtained from the transformed plant according to claim 7, wherein said seed contains said nucleotide sequence in antisense orientation.

10. A method for decreasing theobromine synthesis in a plant, said method comprising introducing into a plant cell double-stranded RNA wherein one strand of said double-stranded RNA encodes a polypeptide encoded by a nucleotide sequence according to any one of claims 1–4, wherein said double-stranded RNA inhibits expression of theobromine synthase, resulting in a decrease of theobromine synthesis from 7-methylxanthine.

11. A transformed plant produced using the method of claim 10.

12. The plant according to claim 11, wherein said plant is selected from the group consisting of *Coffea arabica, Correa canephora, Coffea liberica,* and *Coffea dewevrei.*

13. A method for decreasing theobromine synthesis in a plant, said method comprising introducing into a plant cell the nucleotide sequence according to any one of claims 1–4, wherein transcription of said nucleotide sequence causes a decrease in the expression of theobromine synthase due to co-suppression, resulting in a decrease of theobromine synthesis from 7-methylxanthine.

14. A transformed plant produced using the method of claim 13.

15. The plant according to claim 14, wherein said plant is selected from the group consisting of *Coffea arabica, Correa canephora, Coffea liberica,* and *Coffea dewevrei.*

16. A seed obtained from the transformed plant according to claim 14, wherein said seed contains said nucleotide sequence.

17. A seed obtained from the transformed plant according to claim 15, wherein said seed contains said nucleotide sequence.

* * * * *

UNITED STATES PATENT AND TRADEMARK OFFICE
CERTIFICATE OF CORRECTION

PATENT NO.   : 6,734,342 B2
DATED        : May 11, 2004
INVENTOR(S)  : Hiroshi Sano et al.

It is certified that error appears in the above-identified patent and that said Letters Patent is hereby corrected as shown below:

Column 26,
Line 49, change "plain" to -- plant --.

Signed and Sealed this

Thirtieth Day of November, 2004

JON W. DUDAS
*Director of the United States Patent and Trademark Office*

SEQUENCE LISTING

<160> NUMBER OF SEQ ID NOS: 22

<210> SEQ ID NO 1
<211> LENGTH: 378
<212> TYPE: PRT
<213> ORGANISM: Caffea arabica

<400> SEQUENCE: 1

```
Met Glu Leu Gln Glu Val Leu His Met Asn Glu Gly Glu Gly Asp Thr
 1               5                  10                  15

Ser Tyr Ala Lys Asn Ala Ser Tyr Asn Leu Ala Leu Ala Lys Val Lys
            20                  25                  30

Pro Phe Leu Glu Gln Cys Ile Arg Glu Leu Leu Arg Ala Asn Leu Pro
        35                  40                  45

Asn Ile Asn Lys Cys Ile Lys Val Ala Asp Leu Gly Cys Ala Ser Gly
```

```
                50                  55                  60
Pro Asn Thr Leu Leu Thr Val Arg Asp Ile Val Gln Ser Ile Asp Lys
 65                  70                  75                  80

Val Gly Gln Glu Glu Lys Asn Glu Leu Glu Arg Pro Thr Ile Gln Ile
                 85                  90                  95

Phe Leu Asn Asp Leu Phe Gln Asn Asp Phe Asn Ser Val Phe Lys Leu
                100                 105                 110

Leu Pro Ser Phe Tyr Arg Lys Leu Glu Lys Glu Asn Gly Arg Lys Ile
                115                 120                 125

Gly Ser Cys Leu Ile Ser Ala Met Pro Gly Ser Phe Tyr Gly Arg Leu
130                 135                 140

Phe Pro Glu Glu Ser Met His Phe Leu His Ser Cys Tyr Ser Val His
145                 150                 155                 160

Trp Leu Ser Gln Val Pro Ser Gly Leu Val Ile Glu Leu Gly Ile Gly
                165                 170                 175

Ala Asn Lys Gly Ser Ile Tyr Ser Ser Lys Gly Cys Arg Pro Pro Val
                180                 185                 190

Gln Lys Ala Tyr Leu Asp Gln Phe Thr Lys Asp Phe Thr Thr Phe Leu
                195                 200                 205

Arg Ile His Ser Lys Glu Leu Phe Ser Arg Gly Arg Met Leu Leu Thr
210                 215                 220

Cys Ile Cys Lys Val Asp Glu Phe Asp Glu Pro Asn Pro Leu Asp Leu
225                 230                 235                 240

Leu Asp Met Ala Ile Asn Asp Leu Ile Val Glu Gly Leu Leu Glu Glu
                245                 250                 255

Glu Lys Leu Asp Ser Phe Asn Ile Pro Phe Phe Thr Pro Ser Ala Glu
                260                 265                 270

Glu Val Lys Cys Ile Val Glu Glu Gly Ser Cys Glu Ile Leu Tyr
                275                 280                 285

Leu Glu Thr Phe Lys Ala His Tyr Asp Ala Ala Phe Ser Ile Asp Asp
                290                 295                 300

Asp Tyr Pro Val Arg Ser His Glu Gln Ile Lys Ala Glu Tyr Val Ala
305                 310                 315                 320

Ser Leu Ile Arg Ser Val Tyr Glu Pro Ile Leu Ala Ser His Phe Gly
                325                 330                 335

Glu Ala Ile Met Pro Asp Leu Phe His Arg Leu Ala Lys His Ala Ala
                340                 345                 350

Lys Val Leu His Met Gly Lys Gly Cys Tyr Asn Asn Leu Ile Ile Ser
                355                 360                 365

Leu Ala Lys Lys Pro Glu Lys Ser Asp Val
370                 375

<210> SEQ ID NO 2
<211> LENGTH: 1298
<212> TYPE: DNA
<213> ORGANISM: Caffea arabica

<400> SEQUENCE: 2
agcagtcgca attcgattgt cctgcatatg aatggagctc caagaagtcc tgcatatgaa      60
tgaaggtgaa ggcgatacaa gctacgccaa gaatgcatcc tacaatctgg ctcttgccaa     120
ggtgaaacct ttccttgaac aatgcatacg agaattgttg cgggccaact tgcccaacat     180
caacaagtgc attaaagttg cggatttggg atgcgcttct ggaccaaaca cactttaac     240 agtgcgggac attgtgcaaa gtattgacaa agttggccag gaagagaaga atgaattaga     300
```

-continued

```
acgtcccacc attcagattt ttctgaatga tcttttccaa aatgatttca attcggtttt    360
caagttgctg ccaagcttct accgcaaact cgagaaagaa aatggacgca agataggatc    420
gtgcctaata agcgcaatgc ctggctcttt ctacggcaga ctcttccccg aggagtccat    480
gcattttttg cactcttgtt acagtgttca ttggttatct caggttccca gcggtttggt    540
gattgaattg gggattggtg caaacaaagg gagtatttac tcttccaaag gatgtcgtcc    600
gcccgtccag aaggcatatt tggatcaatt tacgaaagat tttaccacat ttctaaggat    660
tcattcgaaa gagttgtttt cacgtggccg aatgctcctt acctgcattt gtaaagtaga    720
tgaattcgac gaaccgaatc ccctagactt acttgacatg gcaataaacg acttgattgt    780
tgagggactt ctggaggaag aaaaattgga tagtttcaat attccattct ttacaccttc    840
agcagaagaa gtaaagtgca tagttgagga ggaaggttct tgcgaaattt tatatctgga    900
gacttttaag gcccattatg atgctgcctt ctctattgat gatgattacc cagtaagatc    960
ccatgaacaa attaaagcag agtatgtggc atcattaatt agatcagttt acgaacccat   1020
cctcgcaagt catttggag aagctattat gcctgactta ttccacaggc ttgcgaagca   1080
tgcagcaaag gttctccaca tgggcaaagg ctgctataat aatcttatca tttctctcgc   1140
caaaaagcca gagaagtcag acgtgtaaaa gtttgttttt agttggtttt tgtgccgttg   1200
ggggtctttc gggtattgtc gttttgtatt cgtaataaaa gtgatgtgca agaataagat   1260
atttagtaca atattttcat aaaaaaaaaa aaaaaaaa                           1298
```

<210> SEQ ID NO 3
<211> LENGTH: 385
<212> TYPE: PRT
<213> ORGANISM: Caffea arabica

<400> SEQUENCE: 3

```
Met Glu Leu Gln Glu Val Leu His Met Asn Gly Gly Glu Gly Glu Ala
 1               5                  10                  15

Ser Tyr Ala Lys Asn Ser Ser Phe Asn Gln Leu Val Leu Ala Lys Val
            20                  25                  30

Lys Pro Val Leu Glu Gln Cys Val Arg Glu Leu Leu Arg Ala Asn Leu
        35                  40                  45

Pro Asn Ile Asn Lys Cys Ile Lys Val Ala Asp Leu Gly Cys Ala Ser
    50                  55                  60

Gly Pro Asn Thr Leu Leu Thr Val Trp Asp Thr Val Gln Ser Ile Asp
65                  70                  75                  80

Lys Val Lys Gln Glu Met Lys Asn Glu Leu Glu Arg Pro Thr Ile Gln
                85                  90                  95

Val Phe Leu Thr Asp Leu Phe Gln Asn Asp Phe Asn Ser Val Phe Met
            100                 105                 110

Leu Leu Pro Ser Phe Tyr Arg Lys Leu Glu Lys Glu Asn Gly Arg Lys
        115                 120                 125

Ile Gly Ser Cys Leu Ile Ala Ala Met Pro Gly Ser Phe His Gly Arg
    130                 135                 140

Leu Phe Pro Glu Glu Ser Met His Phe Leu His Ser Ser Tyr Ser Leu
145                 150                 155                 160

Gln Phe Leu Ser Gln Val Pro Ser Gly Leu Val Thr Glu Leu Gly Ile
                165                 170                 175

Thr Ala Asn Lys Arg Ser Ile Tyr Ser Ser Lys Ala Ser Pro Pro
            180                 185                 190
```

-continued

```
Val Gln Lys Ala Tyr Leu Asp Gln Phe Thr Lys Asp Phe Thr Thr Phe
        195                 200                 205
Leu Arg Met Arg Ser Glu Glu Leu Leu Ser Arg Gly Arg Met Leu Leu
        210                 215                 220
Thr Cys Ile Cys Lys Gly Asp Glu Cys Asp Gly Pro Asn Thr Met Asp
225                 230                 235                 240
Leu Leu Glu Met Ala Ile Asn Asp Leu Val Ala Glu Gly Arg Leu Gly
                245                 250                 255
Glu Glu Lys Leu Asp Ser Phe Asn Val Pro Ile Tyr Thr Ala Ser Val
            260                 265                 270
Glu Glu Val Lys Cys Met Val Glu Glu Gly Ser Phe Glu Ile Leu
        275                 280                 285
Tyr Leu Gln Thr Phe Lys Leu Arg Tyr Asp Ala Gly Phe Ser Ile Asp
        290                 295                 300
Asp Asp Cys Gln Val Arg Ser His Ser Pro Val Tyr Ser Asp Glu His
305                 310                 315                 320
Ala Arg Ala Ala His Val Ala Ser Leu Ile Arg Ser Val Tyr Glu Pro
                325                 330                 335
Ile Leu Ala Ser His Phe Gly Glu Ala Ile Ile Pro Asp Ile Phe His
            340                 345                 350
Arg Phe Ala Thr Asn Ala Ala Lys Val Ile Arg Leu Gly Lys Gly Phe
        355                 360                 365
Tyr Asn Asn Leu Ile Ile Ser Leu Ala Lys Lys Pro Glu Lys Ser Asp
        370                 375                 380
Ile
385

<210> SEQ ID NO 4
<211> LENGTH: 1360
<212> TYPE: DNA
<213> ORGANISM: Caffea arabica

<400> SEQUENCE: 4
gtcctgcata tgaatggagc tccaagaagt cctgcatatg aatggaggcg aaggcgaagc      60
aagctacgcc aagaattcat ccttcaatca actggttctc gccaaggtga aacctgtcct     120
tgaacaatgc gtacgggaat tgttgcgggc aacttgccc aacatcaaca agtgcattaa     180
agttgcagat ttgggatgcg cttccggacc aaacacactt ttaaccgttt gggacactgt     240
acaaagtatt gacaaagtta agcaagaaat gaagaatgaa ttagaacgtc ccaccattca     300
ggtttttctg actgatcttt tccaaaatga tttcaattcg gttttcatgc tgctgccaag     360
cttctaccgc aaacttgaga agaaaatgg acgcaaaata ggatcgtgcc taatagccgc     420
aatgcctggc tctttccacg gcagactctt ccccgaggag tccatgcatt ttttacactc     480
ttcttacagt cttcagtttt tatcccaggt tcccagcggt ttggtgactg aattggggat     540
cactgcgaac aaaaggagca tttactcttc caaagcaagt cctccgcccg tccagaaggc     600
atatttggat caatttacga aagatttac cacattttta aggatgcgtt cggaagagtt     660
gctttcacgt ggccgaatgc tccttacttg catttgtaaa ggagatgaat gcgacggccc     720
gaataccatg gacttacttg agatggcaat aaacgacttg gttgctgagg gacgtctggg     780
ggaagaaaaa ttggacagtt tcaatgttcc aatctataca gcttcagtag aagaagtaaa     840
gtgcatggtt gaggaggaag ttctttttga aattttatac ttgcagactt ttaagctccg     900
ttatgatgct ggcttctcta ttgatgatga ttgccaagta agatcccatt ccccagtata     960
```

-continued

```
cagcgatgaa catgctagag cagcgcatgt ggcatcatta attagatcag tttacgaacc   1020
catcctagca agtcattttg gagaagctat tatacctgac atattccaca ggtttgcgac   1080
gaatgcagca aaggttatcc gcttgggcaa aggcttctat aataatctta tcatttctct   1140
tgccaaaaaa ccagagaagt cagacatata aaagcttgtt tttagttggt ttttgtgtta   1200
tgggttgttt tctgatacgg ggaaaggatt cagtgcggtt ggggttctat ccgagtattg   1260 tacttttat attattagtt ggtgtataat tattatgtta cattgttata ttcgtaataa    1320
aagtgacgta caaaaataaa atattttcat aaaaaaaaaa                         1360
```

<210> SEQ ID NO 5
<211> LENGTH: 385
<212> TYPE: PRT
<213> ORGANISM: Caffea arabica

<400> SEQUENCE: 5

```
Met Glu Leu Gln Glu Val Leu His Met Asn Gly Gly Glu Gly Asp Ala
 1               5                  10                  15

Ser Tyr Ala Lys Asn Ser Ser Phe Asn Gln Leu Val Leu Ala Lys Val
                20                  25                  30

Lys Pro Val Leu Glu Gln Cys Val Gly Glu Leu Leu Arg Ala Asn Leu
            35                  40                  45

Pro Asn Ile Asn Lys Cys Ile Lys Val Ala Asp Leu Gly Cys Ala Ser
        50                  55                  60

Gly Pro Asn Thr Leu Leu Thr Val Arg Asp Ile Val Gln Ser Ile Asp
 65                  70                  75                  80

Asp Val Arg Gln Glu Met Lys Asn Glu Leu Glu Arg Pro Thr Ile Gln
                85                  90                  95

Val Phe Leu Thr Asp Leu Phe Gln Asn Asp Phe Asn Ser Val Phe Met
            100                 105                 110

Leu Leu Pro Ser Phe Tyr Arg Lys Leu Glu Lys Glu Asn Gly Arg Lys
        115                 120                 125

Ile Gly Ser Cys Leu Ile Ala Ala Met Pro Gly Ser Phe His Gly Arg
    130                 135                 140

Leu Phe Pro Glu Glu Ser Met His Phe Leu His Ser Ser Tyr Ser Leu
145                 150                 155                 160

Gln Phe Leu Ser Gln Val Pro Ser Gly Leu Val Thr Glu Leu Gly Ile
                165                 170                 175

Thr Ala Asn Lys Arg Ser Ile Tyr Ser Ser Lys Ala Ser Pro Pro Pro
            180                 185                 190

Val Gln Lys Ala Tyr Leu Asp Gln Phe Thr Lys Asp Phe Thr Thr Phe
        195                 200                 205

Leu Arg Ile Arg Ser Glu Glu Leu Leu Ser Arg Gly Arg Met Leu Leu
    210                 215                 220

Thr Cys Ile Cys Lys Gly Asp Glu Phe Asp Gly Pro Asn Thr Met Asp
225                 230                 235                 240

Leu Leu Glu Met Ala Ile Asn Asp Leu Val Val Glu Gly His Leu Glu
                245                 250                 255

Glu Glu Lys Leu Asp Ser Phe Asn Val Pro Ile Tyr Ala Ala Ser Val
            260                 265                 270

Glu Glu Leu Lys Cys Ile Val Glu Glu Gly Ser Phe Glu Ile Leu
        275                 280                 285

Tyr Leu Glu Thr Phe Lys Leu Arg Tyr Asp Ala Gly Phe Ser Ile Asp
    290                 295                 300
```

Asp Asp Cys Gln Val Arg Ser His Ser Pro Glu Tyr Ser Asp Glu His
305                 310                 315                 320

Ala Arg Ala Ala His Val Ala Ser Leu Leu Arg Ser Val Tyr Glu Pro
            325                 330                 335

Ile Leu Ala Asn His Phe Gly Glu Ala Ile Ile Pro Asp Ile Phe His
            340                 345                 350

Arg Phe Ala Thr Asn Ala Ala Lys Val Ile Arg Leu Gly Lys Gly Phe
        355                 360                 365

Tyr Asn Asn Leu Ile Ile Ser Leu Ala Lys Lys Pro Glu Lys Ser Asp
    370                 375                 380

Ile
385

<210> SEQ ID NO 6
<211> LENGTH: 1304
<212> TYPE: DNA
<213> ORGANISM: Caffea arabica

<400> SEQUENCE: 6
tttagcagtc ccaattcgat ttatgtacaa gtcctgcata tgaatggagc tccaagaagt      60
cctgcatatg aatggaggcg aaggcgatgc aagctacgcc aagaattcat ccttcaatca    120
actggttctc gccaaggtga aacctgtcct gaacaatgc gtaggggaat gttgcgggc     180 caacttgccc aacatcaaca agtgcattaa agttgcggat tgggatgcg cttccggacc     240 aaacacactt ttaacagttc gggacattgt acaaagtatt gacaaagtta ggcaagaaat    300
gaagaatgaa ttagaacgtc ccaccattca ggttttctg actgatcttt tccaaaatga    360
tttcaattcg gttttcatgt tgctgccaag tttctaccgc aaacttgaga agaaaatgg     420 acgcaagata ggatcgtgcc taatagccgc aatgcctggc tctttccacg gcagactctt    480
ccccgaggag tcaatgcatt ttttacactc ttcttacagt cttcaatttt tatcccaggt    540
tcccagcggt ttggtgactg aattggggat cactgcgaac aaaaggagca tttactcttc    600
caaagcaagt cctccgcccg tccagaaggc atatttggat caatttacga agattttac    660 cacatttta aggattcgtt cggaagagtt gctttcacgc ggccgaatgc tccttactg    720 catttgcaaa ggagatgaat tcgacggccc gaataccatg gacttacttg agatggcaat    780
aaacgacttg gttgttgagg gacatctgga ggaagaaaaa ttggacagtt caatgttcc    840 aatctatgca gcttcagtag aagaattaaa gtgcatagtt gaggaggaag ttcttttga    900 aattttgtac ttggagactt ttaagctccg ttatgatgct ggcttctcta ttgatgatga    960
ttgccaagta agatcccatt ccccagaata cagcgatgaa catgctagag cagcgcatgt   1020
ggcatcatta cttagatcag tttacgaacc catcctcgca aatcattttg gagaagctat   1080
tatacctgac atattccaca ggtttgcgac gaatgcagca aaggttatcc gcttgggcaa   1140
aggcttctat aataatctta tcatttctct tgccaaaaaa ccagagaagt cagacatata   1200
aaagcttgtt tatagttggt ttttgtgcta tggtttgttt tctgatacgg ggaaaggatt   1260
tagtgcggtt ggggttcaaa aaaaaaaaaa aaaaaaaaa aaaa                    1304

<210> SEQ ID NO 7
<211> LENGTH: 372
<212> TYPE: PRT
<213> ORGANISM: Caffea arabica

<400> SEQUENCE: 7

Met Glu Leu Gln Glu Val Leu Arg Met Asn Gly Gly Glu Gly Asp Thr

```
  1               5                  10                 15
Ser Tyr Ala Lys Asn Ser Ala Tyr Asn Gln Leu Val Leu Ala Lys Val
                 20                 25                 30
Lys Pro Val Leu Glu Gln Cys Val Arg Glu Leu Leu Arg Ala Asn Leu
                 35                 40                 45
Pro Asn Ile Asn Lys Cys Ile Lys Val Ala Asp Leu Gly Cys Ala Ser
                 50                 55                 60
Gly Pro Asn Thr Leu Leu Thr Val Arg Asp Ile Val Gln Ser Ile Asp
 65                  70                 75                 80
Lys Val Gly Gln Glu Lys Lys Asn Glu Leu Glu Arg Pro Thr Ile Gln
                 85                 90                 95
Ile Phe Leu Asn Asp Leu Phe Pro Asn Asp Phe Asn Ser Val Phe Lys
                100                105                110
Leu Leu Pro Ser Phe Tyr Arg Lys Leu Glu Lys Glu Asn Gly Arg Lys
                115                120                125
Ile Gly Ser Cys Leu Ile Gly Ala Met Pro Gly Ser Phe Tyr Ser Arg
                130                135                140
Leu Phe Pro Glu Glu Ser Met His Phe Leu His Ser Cys Tyr Cys Leu
145                150                155                160
Gln Trp Leu Ser Gln Val Pro Ser Gly Leu Val Thr Glu Leu Gly Ile
                165                170                175
Ser Thr Asn Lys Gly Ser Ile Tyr Ser Ser Lys Ala Ser Arg Leu Pro
                180                185                190
Val Gln Lys Ala Tyr Leu Asp Gln Phe Thr Lys Asp Phe Thr Thr Phe
                195                200                205
Leu Arg Ile His Ser Glu Glu Leu Phe Ser His Gly Arg Met Leu Leu
                210                215                220
Thr Cys Ile Cys Lys Gly Val Glu Leu Asp Ala Arg Asn Ala Ile Asp
225                230                235                240
Leu Leu Glu Met Ala Ile Asn Asp Leu Val Val Glu Gly His Leu Glu
                245                250                255
Glu Glu Lys Leu Asp Ser Phe Asn Leu Pro Val Tyr Ile Pro Ser Ala
                260                265                270
Glu Glu Val Lys Cys Ile Val Glu Glu Gly Ser Phe Glu Ile Leu
                275                280                285
Tyr Leu Glu Thr Phe Lys Val Leu Tyr Asp Ala Gly Phe Ser Ile Asp
290                295                300
Asp Glu His Ile Lys Ala Glu Tyr Val Ala Ser Ser Val Arg Ala Val
305                310                315                320
Tyr Glu Pro Ile Leu Ala Ser His Phe Gly Glu Ala Ile Ile Pro Asp
                325                330                335
Ile Phe His Arg Phe Ala Lys His Ala Ala Lys Val Leu Pro Leu Gly
                340                345                350
Lys Gly Phe Tyr Asn Asn Leu Ile Ile Ser Leu Ala Lys Lys Pro Glu
                355                360                365
Lys Ser Asp Val
        370

<210> SEQ ID NO 8
<211> LENGTH: 1316
<212> TYPE: DNA
<213> ORGANISM: Caffea arabica

<400> SEQUENCE: 8
```

```
ctttggcagt cccaatttga tttatgtaca agtcctgcat atgaatggag ctccaagaag      60
tcctgcggat gaatggaggc gaaggcgata caagctacgc caagaattca gcctacaatc     120
aactggttct cgccaaggtg aaacctgtcc ttgaacaatg cgtacgggaa ttgttgcggg     180
ccaacttgcc caacatcaac aagtgcatta agttgcgga tttgggatgc gcttctggac      240
caaacacact tttaacagtt cgggacattg tccaaagtat tgacaaagtt ggccaggaaa     300
agaagaatga attagaacgt cccaccattc agattttct gaatgatctt ttcccaaatg      360
atttcaattc ggttttcaag ttgctgccaa gcttctaccg caaacttgag aaagaaaatg     420
gacgcaaaat aggatcgtgc ctaatagggg caatgcccgg ctctttctac agcagactct     480
tccccgagga gtccatgcat tttttacact cttgttactg tcttcaatgg ttatctcagg     540
ttcctagcgg tttggtgact gaattgggga tcagtacgaa caagggagc atttactctt      600 ccaaagcaag tcgtctgccc gtccagaagg catatttgga tcaatttacg aaagatttta     660
ccacatttct aaggattcat tcggaagagt tgttttcaca tggccgaatg ctccttactt     720
gcatttgtaa aggagttgaa ttagacgccc ggaatgccat agacttactt gagatggcaa     780
taaacgactt ggttgttgag ggacatctgg aggaagaaaa attggatagt ttcaatcttc     840
cagtctatat accttcagca gaagaagtaa agtgcatagt tgaggaggaa ggttcttttg     900 aaatttata cctggagact tttaaggtcc tttacgatgc tggcttctct attgacgatg      960
aacatattaa agcagagtat gttgcatctt ccgttagagc agtttacgaa cccatcctcg    1020
caagtcattt tggagaagct attataccctg acatattcca caggtttgcg aagcatgcag   1080
caaaggttct cccccttgggc aaaggcttct ataataatct tatcatttct ctcgccaaaa    1140
agccagagaa gtcagacgtg taaaagtttg tttttgtgtt ggggaaagga ataagtgccg    1200
ttgggggtct ttcgggtatt gtgcttttta tattatattg ttttgtatcc gtaataaaag    1260
tggtgtgtaa gaataagata tttgacatat attattttca aaaaaaaaa aaaaaa         1316
```

<210> SEQ ID NO 9
<211> LENGTH: 23
<212> TYPE: DNA
<213> ORGANISM: Artificial Sequence
<220> FEATURE:
<223> OTHER INFORMATION: forward primer
<220> FEATURE:
<221> NAME/KEY: misc_feature
<222> LOCATION: 3,9,12,15,18
<223> OTHER INFORMATION: n = inosine

<400> SEQUENCE: 9
ggntgydsnd snggnccnaa yac                                               23

<210> SEQ ID NO 10
<211> LENGTH: 23
<212> TYPE: DNA
<213> ORGANISM: Artificial Sequence
<220> FEATURE:
<223> OTHER INFORMATION: reverse primer
<220> FEATURE:
<221> NAME/KEY: misc_feature
<222> LOCATION: 3,6,15,18,21
<223> OTHER INFORMATION: n = inosine

<400> SEQUENCE: 10
arnyknyyrt rraanswncc ngg                                               23

<210> SEQ ID NO 11
<211> LENGTH: 8

```
<212> TYPE: PRT
<213> ORGANISM: Arabidopsis thaliana

<400> SEQUENCE: 11

Gly Cys Ala Ala Gly Pro Asn Thr
1               5

<210> SEQ ID NO 12
<211> LENGTH: 8
<212> TYPE: PRT
<213> ORGANISM: Arabidopsis thaliana

<400> SEQUENCE: 12

Gly Cys Ala Ser Gly Pro Asn Thr
1               5

<210> SEQ ID NO 13
<211> LENGTH: 8
<212> TYPE: PRT
<213> ORGANISM: Arabidopsis thaliana

<400> SEQUENCE: 13

Gly Cys Ser Ala Gly Pro Asn Thr
1               5

<210> SEQ ID NO 14
<211> LENGTH: 8
<212> TYPE: PRT
<213> ORGANISM: Arabidopsis thaliana

<400> SEQUENCE: 14

Gly Cys Ser Ser Gly Pro Asn Thr
1               5

<210> SEQ ID NO 15
<211> LENGTH: 9
<212> TYPE: PRT
<213> ORGANISM: Arabidopsis thaliana

<400> SEQUENCE: 15

Pro Gly Ser Phe His Gly Arg Leu Phe
1               5

<210> SEQ ID NO 16
<211> LENGTH: 9
<212> TYPE: PRT
<213> ORGANISM: Arabidopsis thaliana

<400> SEQUENCE: 16

Pro Gly Ser Phe His Lys Arg Leu Phe
1               5

<210> SEQ ID NO 17
<211> LENGTH: 9
<212> TYPE: PRT
<213> ORGANISM: Arabidopsis thaliana

<400> SEQUENCE: 17

Pro Gly Ser Phe His Gly Asn Leu Phe
1               5

<210> SEQ ID NO 18
<211> LENGTH: 9
<212> TYPE: PRT
<213> ORGANISM: Arabidopsis thaliana
```

-continued

```
<400> SEQUENCE: 18

Pro Gly Ser Phe His Lys Asn Leu Phe
1               5

<210> SEQ ID NO 19
<211> LENGTH: 9
<212> TYPE: PRT
<213> ORGANISM: Arabidopsis thaliana

<400> SEQUENCE: 19

Pro Gly Ser Phe Tyr Gly Arg Leu Phe
1               5

<210> SEQ ID NO 20
<211> LENGTH: 9
<212> TYPE: PRT
<213> ORGANISM: Arabidopsis thaliana

<400> SEQUENCE: 20

Pro Gly Ser Phe Tyr Lys Arg Leu Phe
1               5

<210> SEQ ID NO 21
<211> LENGTH: 9
<212> TYPE: PRT
<213> ORGANISM: Arabidopsis thaliana

<400> SEQUENCE: 21

Pro Gly Ser Phe Tyr Gly Asn Leu Phe
1               5

<210> SEQ ID NO 22
<211> LENGTH: 9
<212> TYPE: PRT
<213> ORGANISM: Arabidopsis thaliana

<400> SEQUENCE: 22

Pro Gly Ser Phe Tyr Lys Asn Leu Phe
1               5
```